United States Patent

Nishimori et al.

(10) Patent No.: US 9,604,959 B2
(45) Date of Patent: Mar. 28, 2017

(54) THIOL COMPOUND AND COMPOSITION FOR OPTICAL MATERIALS USING THE SAME

(71) Applicant: MITSUBISHI GAS CHEMICAL COMPANY, INC., Tokyo (JP)

(72) Inventors: Yoshihiko Nishimori, Tokyo (JP); Teruo Kamura, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 68 days.

(21) Appl. No.: 14/431,029

(22) PCT Filed: Dec. 8, 2014

(86) PCT No.: PCT/JP2014/082377
§ 371 (c)(1),
(2) Date: Mar. 25, 2015

(87) PCT Pub. No.: WO2015/087822
PCT Pub. Date: Jun. 18, 2015

(65) Prior Publication Data
US 2016/0060244 A1 Mar. 3, 2016

(30) Foreign Application Priority Data
Dec. 11, 2013 (JP) ................. 2013-256008

(51) Int. Cl.
C07D 341/00 (2006.01)
C08G 18/38 (2006.01)
G02B 1/04 (2006.01)

(52) U.S. Cl.
CPC ....... *C07D 341/00* (2013.01); *C08G 18/3876* (2013.01); *G02B 1/041* (2013.01); *G02B 1/04* (2013.01)

(58) Field of Classification Search
CPC .............. C07D 341/00; G02B 1/041
See application file for complete search history.

(56) References Cited

U.S. PATENT DOCUMENTS

| | | |
|---|---|---|
| 5,087,758 A | 2/1992 | Kanemura et al. |
| 5,326,501 A | 7/1994 | Ohkubo et al. |
| 6,117,923 A | 9/2000 | Amagai et al. |

FOREIGN PATENT DOCUMENTS

| | | |
|---|---|---|
| CN | 103145944 | 6/2013 |
| EP | 0 665 219 A1 † | 8/1995 |
| EP | 1 316 819 A1 † | 6/2003 |
| EP | 1326095 | 7/2003 |
| EP | 1369709 | 12/2003 |
| EP | 1518873 | 3/2005 |
| EP | 2 011 785 A1 † | 1/2009 |
| EP | 2 065 415 A1 † | 6/2009 |
| EP | 2821428 | 1/2015 |
| EP | 2894177 | 7/2015 |
| JP | 2-270859 | 11/1990 |
| JP | 3-236386 | 10/1991 |
| JP | 07-118390 A † | 5/1995 |
| JP | 9-110955 | 4/1997 |
| JP | 10-298287 | 11/1998 |
| JP | 2004-175726 | 6/2004 |
| JP | 2004-175726 A † | 6/2004 |
| JP | 2004175726 * | 6/2004 |
| WO | 03/002632 | 1/2003 |
| WO | 2015/064548 | 5/2015 |

OTHER PUBLICATIONS

European Office Action issued in European Patent Appl. No. 14 869 858.2, dated May 3, 2016.
Search report from PCT/JP2014/082377, mail date is Jan. 27, 2015.
Extended European Search Report issued by European patent office in Patent Application No. 14869858.2, dated Oct. 22, 2015.
Goodrow, Marvin H. and W. Kenneth Musker, Synthesis of Medium Ring Disulfides by Titrimetry; An Improvement on High Dilution Techniques, Selected Sections of pp. 457-459, Jun. 1981, Georg Thieme Verlag, New York.†

\* cited by examiner
† cited by third party

*Primary Examiner* — Monique Peets
(74) *Attorney, Agent, or Firm* — Greenblum & Bernstein, P.L.C.

(57) ABSTRACT

According to the present invention, it is possible to provide a thiol compound represented by formula (1):

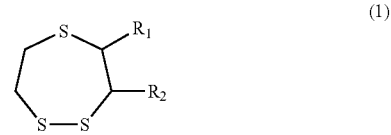

(1)

wherein $R_1$ is $CH_2SCH_2CH_2SH$, and $R_2$ is hydrogen.
In addition, according to the present invention, it is possible to provide a mixture of the thiol compound and 4-mercaptomethyl-1,8-dimercapto-3,6-dithiaoctane, wherein the ratio of the thiol compound is 0.001 to 5.0% by mass.

7 Claims, 2 Drawing Sheets

THIOL COMPOUND AND COMPOSITION FOR OPTICAL MATERIALS USING THE SAME

TECHNICAL FIELD

The present invention relates to a thiol compound suitably used for optical materials such as a plastic lens, a prism, an optical fiber, an information recording substrate and a filter, in particular a plastic lens, and a composition for optical materials using the same.

BACKGROUND ART

Plastic lenses are lightweight, highly tough and easy to be dyed. Properties particularly required for plastic lenses are: low specific gravity; high transparency; low yellowness; high refractive index and high Abbe number as optical properties; high heat resistance; high strength; and the like. A high refractive index allows a lens to be thinner, and a high Abbe number reduces the chromatic aberration of a lens.

Recently, as raw materials for plastic lenses for eyeglasses, many organic compounds having a sulfur atom have been reported. Among such compounds, polythiol compounds having a sulfur atom are, for example, reacted with an isocyanate to be used as polythiourethane resins excellent in impact resistance, or reacted with an episulfide to be used as resins having an excellent refractive index, and thus well known as useful compounds (Patent Documents 1 and 2). Among them, 4-mercaptomethyl-1,8-dimercapto-3,6-dithiaoctane is a typical compound (Patent Document 3).

PRIOR ART DOCUMENTS

Patent Documents

Patent Document 1: Japanese Laid-Open Patent Publication No. H02-270859
Patent Document 2: Japanese Laid-Open Patent Publication No. H10-298287
Patent Document 3: Japanese Laid-Open Patent Publication No. H09-110955

SUMMARY OF THE INVENTION

Problems to be Solved by the Invention

However, in the case of a resin obtained from a composition for optical materials comprising this compound, optical distortion tends to occur in tightly curved lenses. In optical applications, products in which distortion occurs are regarded as defective products, the yield of obtained resin is significantly reduced, and it is economically disadvantageous. Therefore, the improvement thereof is desired.

Specifically, the problem to be solved by the present invention is to provide a composition for optical materials free of distortion with respect to resins obtained with use of 4-mercaptomethyl-1,8-dimercapto-3,6-dithiaoctane.

Means for Solving the Problems

Under such circumstances, the present inventors diligently made researches and found that the aforementioned problems can be solved by a compound represented by formula (1) below, and thus the present invention was achieved. Specifically, the present invention is as follows:
[1] A thiol compound represented by formula (1):

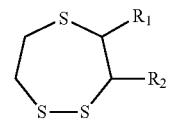

wherein $R_1$ is $CH_2SCH_2CH_2SH$ and $R_1$ is hydrogen.

[2] A method for producing the thiol compound represented by formula (1) according to item [1], comprising subjecting SH groups in 4-mercaptomethyl-1,8-dimercapto-3,6-dithiaoctane which is a compound represented by formula (2) to disulfidation by means of an intramolecular reaction using a halogen compound and a basic compound:

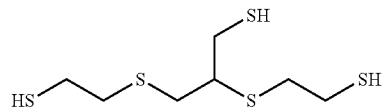

[3] A mixture of the thiol compound according to item [1] and a compound represented by formula (2), wherein the ratio of the thiol compound according to item [1] is 0.001 to 5.0% by mass:

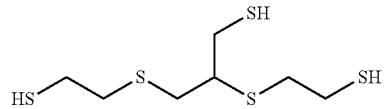

[4] A composition for optical materials, which comprises the mixture according to item[3] and at least one of a polyisocyanate compound and an episulfide compound.
[5] A method for producing an optical material, which comprises adding a polymerization catalyst to the composition for optical materials according to item [4] in an amount of 0.0001 to 10% by mass relative to the total amount of the composition for optical materials to polymerize and cure the composition.
[6] An optical material obtained by the production method according to item [5].
[7] An optical lens comprising the optical material according to item [6].

Advantageous Effect of the Invention

According to the present invention, it is possible to provide a composition for optical materials free of distortion with respect to resins obtained with use of 4-mercaptomethyl-1,8-dimercapto-3,6-dithiaoctane.

EMBODIMENTS FOR CARRYING OUT THE INVENTION

Figure 1:
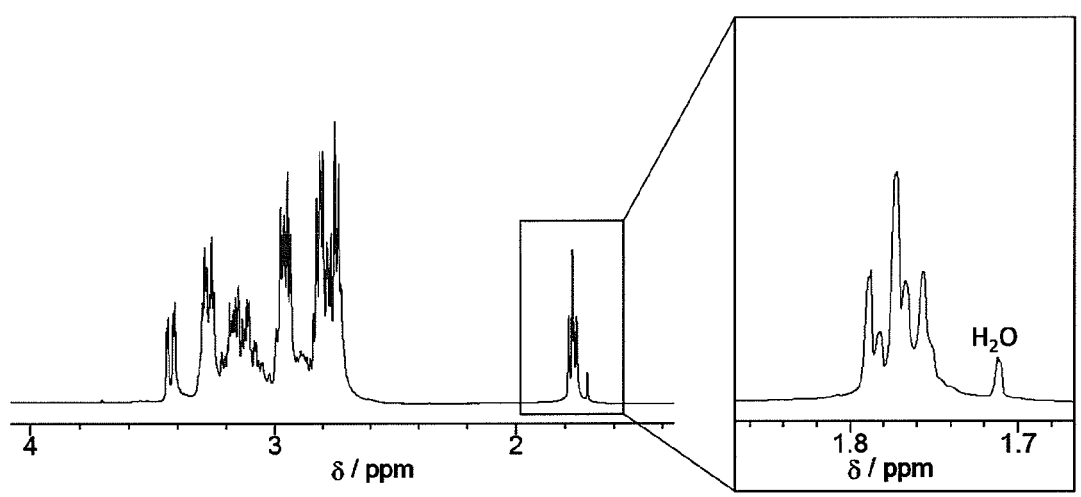
FIG. 1 shows results of 1H-NMR analysis of the compound represented by formula (1).

The present invention relates to a compound represented by formula (1) above and a mixture of the compound represented by formula (1) and a compound represented by formula (2) above, wherein the ratio of the compound represented by formula (1) is 0.001 to 5.0% by mass.

Hereinafter, the compound of the present invention, i.e., the compound represented by formula (1) will be described in detail.

In the present invention, the compound represented by formula (1) above is used. Compounds of formula (1) may be used solely, or two of them may be used in combination.

As the method for producing the compound represented by formula (1) of the present invention, it is easiest to use the compound of formula (2) as a starting material.

SH groups in the compound of formula (2) are subjected to disulfidation by means of an intramolecular reaction using a halogen compound and a basic compound. Specific examples of the halogen compound to be used for disulfidation are chlorine, bromine and iodine, but preferred are bromine and iodine. The amount of the halogen compound to be used is 0.1 to 5 mol relative to 1 mol of the compound represented by formula (2). The amount is preferably 0.2 to 3 mol, and more preferably 0.3 to 1 mol. When the amount is less than 0.1 mol, larger amounts of unreacted raw materials remain, and when the amount is more than 5 mol, the yield is reduced due to oligomerization and therefore it is economically undesirable.

Specific examples of the basic compound are sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide. Preferred are sodium carbonate, potassium carbonate, magnesium carbonate, calcium carbonate, sodium hydrogen carbonate and potassium hydrogen carbonate.

The amount of the basic compound to be used is 0.1 to 10 mol relative to 1 mol of the compound represented by formula (2). The amount is preferably 0.2 to 5 mol, and more preferably 0.3 to 3 mol. When the amount is less than 0.1 mol or more than 10 mol, larger amounts of unreacted raw materials remain, and therefore it is economically undesirable.

A solvent may be used but does not have to be used. When using a solvent, water, alcohols, ethers, ketones, aromatic hydrocarbons and halogenated hydrocarbons can be used. Specific examples thereof include water, methanol, ethanol, propanol, isopropanol, diethyl ether, tetrahydrofuran, dioxane, methyl cellosolve, ethyl cellosolve, butyl cellosolve, methyl ethyl ketone, acetone, benzene, toluene, xylene, dichloromethane, chloroform and chlorobenzene. Among them, preferred are water, methanol, ethanol, toluene, dichloromethane and chloroform, and most preferred are methanol, ethanol and toluene.

The reaction temperature is not particularly limited as long as it is for reaction progress, but is preferably −10 to 150° C., more preferably 0 to 120° C., and even more preferably 10 to 100° C. The reaction time is not particularly limited, but is usually 20 hours or less. When the reaction temperature is lower than −10° C., the reaction does not proceed or proceed too slowly and it is undesirable. When the reaction temperature is higher than 150° C., oligomerization occurs, resulting in a high molecular weight and it is undesirable.

The compound represented by formula (1) obtained in this way is used together with the compound represented by formula (2) to provide a composition for optical materials.

The present invention relates to a mixture of the compound represented by formula (1) and the compound represented by formula (2), wherein the ratio of the compound represented by formula (1) is 0.001 to 5.0% by mass. The ratio of the compound represented by formula (1) is preferably 0.005 to 3.0% by mass, and more preferably 0.01 to 1.5% by mass. When the ratio of the compound represented by formula (1) is less than 0.001% by mass, effects exerted may be insufficient, and when the ratio is more than 5.0% by mass, the heat resistance may be reduced.

The composition for optical materials of the present invention comprises the aforementioned mixture of the compound represented by formula (1) and the compound represented by formula (2) and a polyisocyanate compound and/or an episulfide compound.

Polyisocyanate compounds to be used for the composition for optical materials of the present invention may be used solely, or two or more of them may be used in combination.

Specific examples thereof include diethylene diisocyanate, tetramethylene diisocyanate, hexamethylene diisocyanate, trimethylhexamethylene diisocyanate, cyclohexane diisocyanate, 1,3-bis(isocyanatemethyl)cyclohexane, 1,4-bis(isocyanatemethyl)cyclohexane, isophorone diisocyanate, 2,6-bis(isocyanatemethyl)decahydronaphthalene, lysine triisocyanate, tolylene diisocyanate, o-tolidine diisocyanate, diphenylmethane diisocyanate, diphenylether diisocyanate, 3-(2'-isocyanatecyclohexyl)propylisocyanate, isopropylidene bis(cyclohexyl isocyanate), 2,2'-bis(4-isocyanatephenyl)propane, triphenylmethane triisocyanate, bis(diisocyanatetolyl)phenylmethane, 4,4',4''-triisocyanate-2,5-dimethoxyphenylamine, 3,3'-dimethoxybenzidine-4,4'-diisocyanate, 1,3-phenylene diisocyanate, 1,4-phenylene diisocyanate, 4,4'-diisocyanatebiphenyl, 4,4'-diisocyanate-3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylene diisocyanate, p-xylylene diisocyanate, m-tetramethyl xylylene diisocyanate, p-tetramethyl xylylene diisocyanate, 1,3-bis(2-isocyanate-2-propyl)benzene, 2,6-bis(isocyanatemethyl)naphthalene, 1,5-naphthalene diisocyanate, bis(isocyanatemethyl)tetrahydrodicyclopentadiene, bis(isocyanatemethyl)dicyclopentadiene, bis(isocyanatemethyl)tetrahydrothiophene, bis(isocyanatemethyl)norbornene, bis(isocyanatemethyl)adamantane, thiodiethyl diisocyanate, thiodipropyi diisocyanate, thiodihexyl diisocyanate, bis[(4-isocyanatemethyl)phenyl]sulfide, 2,5-diisocyanate-1,4-dithiane, 2,5-diisocyanatemethyl-1,4-dithiane, 2,5-diisocyanatemethylthiophene, dithiodiethyl diisocyanate and dithiodipropyl diisocyanate.

However, the polyisocyanate compound targeted by the present invention is not limited to the above-described examples, and these compounds may be used solely, or two or more of them may be used in combination.

Among them, at least one compound selected from isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(isocyanatemethyl)cyclohexane, 1,4-bis(isocyanatemethyl)cyclohexane, bis(isocyanatemethyl)norbornene and 2,5-diisocyanatemethyl-1,4-dithiane is a preferred specific example. Isophorone diisocyanate, tolylene diisocyanate, diphenylmethane diisocyanate, hexamethylene diisocyanate, 1,3-bis(isocyanatemethyl)cyclohexane and m-xylylene diisocyanate are particularly preferred, and isophorone diisocyanate, m-xylylene diisocyanate and 1,3-bis(isocyanatemethyl)cyclohexane are most preferred.

Further, the ratio of the SH groups in the thiol compound to the NCO groups in the polyisocyanate compound, i.e., (SH group/NCO group) is preferably 0.8 to 2.5, more preferably 0.9 to 2.25, and even more preferably 0.95 to 2.0. When the above-described ratio is less than 0.8, a lens may turn yellow at the time of molding, and when the ratio is more than 2.5, the heat resistance may be reduced.

Examples of the episulfide compound to be used in the present invention include episulfides such as bis(β-epithiopropyl)sulfide, bis(β-epithiopropyedisulfide, bisβ-epithiopropylthio)methane, 1,2-bis(β-epithiopropylthio)ethane, 1,3-bis(β-epithiopropylthio)propane and 1,4-bis(β-epithiopropylthio)butane. Such compounds may be used solely, or two or more compounds may be used in combination.

However, the episulfide compound to be used in the present invention is not limited to the above-described examples, and these compounds may be used solely, or two or more of them may be used in combination.

Among the above-described compounds, bis(β-epithiopropyl)sulfide and bis(β-epithiopropyl)disulfide are preferred, and bis(β-epithiopropyl)sulfide is most preferred.

In the present invention, other polythiol compounds may be used for combined use. Polythiol compounds may be used solely, or two or more of them may be used in combination.

Specific examples thereof include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethylthio)-1,3-dimercaptopropane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycol bis(2-mercaptoacetate), ethyleneglycol bis(3-mercaptopropionate), diethyleneglycol bis(2-mercaptoacetate), diethyleneglycol bis(3-mercaptopropionate), 1,4-butanediol bis(2-mercaptoacetate), 1,4-butanediol bis(3-mercaptopropionate), trimethylolpropane tris(thioglycolate), trimethylolpropane tris(mercapto propionate), pentaerythritol tetrakis-thioglycolate, pentaerythritol tetrakis-mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5-dimercaptomethylthiophene, 1,2-dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol and 1,1,3,3-tetrakis(mercaptomethylthio)propane.

Among them, bis(2-mercaptoethyl)sulfide, 2,5-dimercaptomethyl-1,4-dithiane, 1,3-bis(mercaptomethyl)benzene, 1,4-bis(mercaptomethyl)benzene, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, pentaerythritol tetrakis-mercaptopropionate, pentaerythritol tetrakis-thioglycolate, trimethylolpropane tris(thioglycolate) and trimethylolpropane tris(mercapto propionate) are preferred, bis(2-mercaptoethyl)sulfide, 2,5-bis(2-mercaptomethyl)-1,4-dithiane, 1,3-bis(mercaptomethyl)benzene, pentaerythritol tetrakis-mercaptopropionate and pentaerythritol tetrakis-thioglycolate are more preferred, and bis(2-mercaptoethyl)sulfide and 2,5-dimercaptomethyl-1,4-dithiane are most preferred.

When obtaining an optical material by polymerizing and curing the composition for optical materials of the present invention, it is preferred to add a polymerization catalyst. As the polymerization catalyst, publicly-known urethanation catalysts and episulfide polymerization catalysts can be used. Preferred are organotins, amines, phosphines and onium salts. Particularly preferred are organotins and onium salts, and among them, organotins, quaternary ammonium salts and quaternary phosphonium salts are preferred.

The amount of the polymerization catalyst to be added cannot be determined categorically because it varies depending on the components of the composition, the mixing ratio and the method for polymerization and curing, but the amount is usually 0.0001% by mass to 10% by mass, preferably 0.001% by mass to 5% by mass, more preferably 0.01% by mass to 1% by mass, and most preferably 0.01% by mass to 0.5% by mass relative to 100% by mass of the total of the composition for optical materials. When the amount of the polymerization catalyst to be added is more than 10% by mass, the composition may be rapidly polymerized. When the amount of the polymerization catalyst to be added is less than 0.0001% by mass, the composition for optical materials may be insufficiently cured, resulting in poor heat resistance.

Moreover, in the production of the optical material according to the production method of the present invention, it is surely possible to add additives such as an ultraviolet absorber, a blueing agent and a pigment to the composition for optical materials to further improve practicability of the optical material obtained.

Preferred examples of the ultraviolet absorber include benzotriazole-based compounds, and particularly preferred are 2-(2-hydroxy-5-methylphenyl)-2H-benzotriazol, 5-chloro-2-(3,5-di-tert-butyl-2-hydroxyphenyl)-2H-benzotriazol, 2-(2-hydroxy-4-octylphenyl)-2H-benzotriazol, 2-(2-hydroxy-4-methoxyphenyl)-2H-benzotriazol, 2-(2-hydroxy-4-ethoxyphenyl)-2H-benzotriazol, 2-(2-hydroxy-4-butoxyphenyl)-2H-benzotriazol, 2-(2-hydroxy-4-octyloxyphenyl)-2H-benzotriazol and 2-(2-hydroxy-5-t-octylphenyl)-2H-benzotriazol.

The amount of the ultraviolet absorber to be added is usually 0.01 to 5% by mass relative to 100% by mass of the total of the composition for optical materials.

When polymerizing and curing the composition for optical materials, publicly-known additives such as an internal mold release agent, an antioxidant and a polymerization modifier may be added according to need.

The composition for optical materials thus obtained is injected into a mold or the like and polymerized to obtain an optical material.

At the time of cast-molding the composition for optical materials of the present invention, it is preferred to filter and remove impurities using, for example, a filter having a pore diameter of about 0.1 to 5 μm in terms of improving the quality of the optical material of the present invention.

The composition for optical materials of the present invention is usually polymerized as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps.

Further, it is preferred to anneal the obtained optical material at a temperature of 50 to 150° C. for about 10 minutes to 5 hours after curing is completed in terms of eliminating distortion of the optical material of the present invention. Moreover, the obtained optical material may be subjected to a surface treatment such as dyeing, hard coating, impact-resistant coating, antireflection treatment and imparting antifog properties according to need.

The optical material of the present invention can be suitably used as an optical lens.

EXAMPLES

Hereinafter, the present invention will be specifically described by way of working examples and comparative examples. However, the present invention is not limited to the below-described working examples.

1. 1H-NMR measurement

The measurement was carried out using JNM-LA500 manufactured by JEOL Ltd.

2. Mass spectrometry

The measurement was carried out according to the ionization method EI using HP6890/MS5973 which is a gas chromatograph mass spectrometer manufactured by Agilent Technologies, in which DB-5MS (Agilent Technologies) is attached to a capillary column.

3. Infrared spectroscopy

The measurement was carried out using FT/IR-4200 manufactured by JASCO Corporation with ATR PRO450-S being attached thereto.

4. Method for quantitating the compound of formula (1)

The quantitation was carried out according to the absolute calibration curve method using a capillary gas chromatograph (manufactured by Shimadzu Corporation, GC2010, detector: hydrogen flame ionization detector (FID)), in which DB-5MS (Agilent Technologies) is attached to a capillary column.

5. Distortion

A composition for optical materials was injected into a −15D lens mold having a diameter of 70 mm composed of two glass plates and a tape to be polymerized and cured. After cooling, the obtained product was released from the mold and annealed, and after that, it was visually observed using a high pressure mercury vapor lamp. 10 products were produced, and the case where no distortion was observed regarding 10 products was rated as "A", the case where distortion was observed regarding 1 product was rated as "B", the case where distortion was observed regarding 2 products was rated as "C", and the case where distortion was observed regarding 3 or more products was rated as "D". A, B and C are regarded as acceptable, but A and B are preferred, and A is particularly preferred.

Example 1

Figure 2:
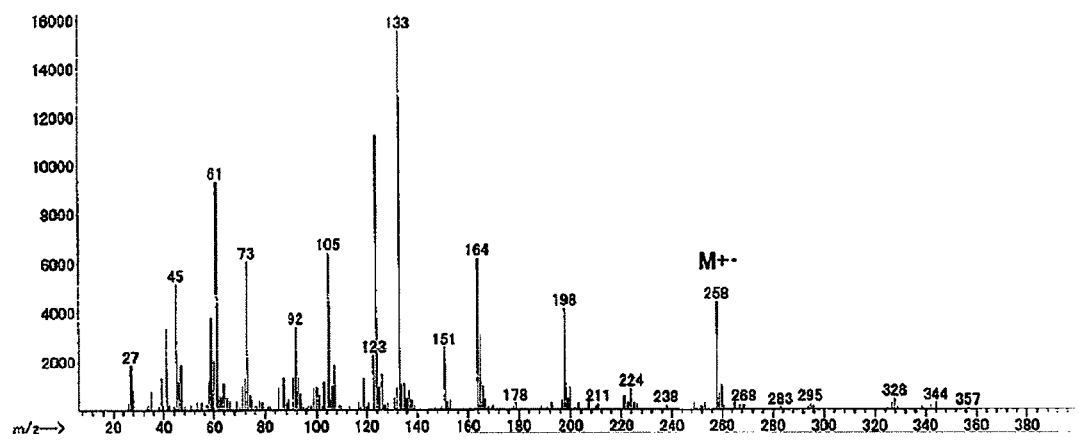
FIG. 2 shows results of mass spectrometry of the compound represented by formula (1).
Figure 3:
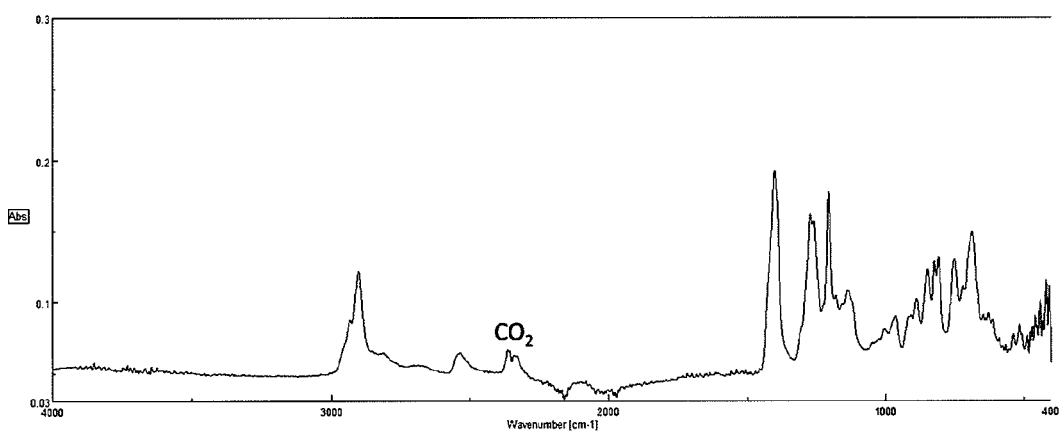
FIG. 3 shows results of infrared spectroscopy of the compound represented by formula (1).

13.2 parts by mass of the compound represented by formula (2) and 5.5 parts by mass of sodium carbonate were put into a 300 mL four-neck reaction flask equipped with a stirrer, a reflux cooling tube, a nitrogen gas purge tube and a thermometer. A solution obtained by dissolving 10.3 parts by mass of iodine in 80 parts by mass of ethanol was added dropwise thereto at 10° C. over 30 minutes. Next, 50 parts by mass of chloroform was added thereto, and the mixture was washed with an acid and washed with water, and the solvent was removed under reduced pressure with heating. To the obtained reaction product, a solution obtained by dissolving 90 parts by mass of toluene and 0.2 parts by mass of potassium hydroxide in 5 parts by mass of methanol was added, and the mixture was heated to reflux for 90 minutes. The toluene solution was washed with an acid and washed with water, and toluene was removed under reduced pressure with heating. The obtained reaction product was purified by means of silica gel column chromatography, thereby obtaining 5.0 parts by mass of the compound represented by formula (1). The results of 1H-NMR analysis (FIG. 1), mass spectrometry (FIG. 2) and infrared spectroscopy (FIG. 3) are shown below. 1H-NMR spectrum (CDCl3): δ=1.77 (1H), 2.7-3.5 (13H)

|  | (analysis value) | (calculation value) |
| --- | --- | --- |
| Mass spectrum (EI): | 258 | 258 |

Infrared absorption spectrum: 2535 cm-1 (characteristic absorption of mercaptan)

Example 2

The compound represented by formula (1) obtained in Example 1 was mixed with the compound represented by formula (2), and mixtures of the compound represented by formula (1) and the compound represented by formula (2), in which the respective ratios of the compound represented by formula (1) are 0.001, 0.005, 0.01, 1.5, 3.0 and 5.0% by mass, were obtained.

Examples 3-8 and Comparative Example 1

0.015 parts by mass of dibutyltin dichloride as a curing catalyst and 0.10 parts by mass of dioctyl phosphate were mixed with and dissolved in 52 parts by mass of 1,3-bis (isocyanatemethyl)benzene at 10 to 15° C. Further, 48 parts by mass of the mixture of Example 2 comprising 4-mercaptomethyl-1,8-dimercapto-3,6-dithiaoctane as the main component was mixed therewith to obtain a homogeneous solution. This homogeneous mixture was defoamed under 600 Pa for 1 hour, and after that, it was filtered using a PTFE filter of 1 μm, injected into a +5D mold having a diameter of 70 mm, polymerized at a temperature of from 40° C. to 130° C. over 24 hours, and then released from the mold. In this way, optical materials of Examples 3-8 were obtained.

The process was carried out in a manner similar to that in Example 3, except that a mixture of the compound represented by formula (1) and the compound represented by formula (2), in which the ratio of the compound represented by formula (1) is 10.0% by mass, was used instead of the mixture of Example 2 comprising 4-mercaptomethyl-1,8-dimercapto-3,6-dithiaoctane as the main component, thereby obtaining an optical material of Comparative Example 1. The results are shown in Table 1.

TABLE 1

| Examples | Mixture (parts by mass) | Ratio of (1) in the mixture (% by mass) | Isocyanate (parts by mass) | Distortion |
|---|---|---|---|---|
| Example 3 | 48.0 | 0.001 | 52.0 | C |
| Example 4 | 48.0 | 0.005 | 52.0 | B |
| Example 5 | 48.0 | 0.01 | 52.0 | A |
| Example 6 | 48.0 | 1.5 | 52.0 | A |
| Example 7 | 48.0 | 3.0 | 52.0 | B |
| Example 8 | 48.0 | 5.0 | 52.0 | C |
| Comparative Example 1 | 48.0 | 10.0 | 52.0 | D |

Examples 9-14 and Comparative Example 2

To 77 parts by mass of bis(β-epithiopropyl)sulfide, 9 parts by mass of 1,3-bis(isocyanatemethyl)benzene and 14 parts by mass of the mixture of Example 2 comprising 4-mercaptomethyl-1,8-dimercapto-3,6-dithiaoctane as the main component, 0.2 parts by mass of tetrabutylphosphonium bromide as a polymerization catalyst and 0.05 parts by mass of dibutyltin dichloride were added to produce a homogeneous solution at room temperature. This homogeneous mixture was defoamed under 600 Pa for 1 hour, and after that, it was filtered using a PTFE filter of 1 μm, injected into a +5D mold having a diameter of 70 mm, heated from 20° C. to 100° C. over 20 hours to be polymerized and cured, and then released from the mold. In this way, optical materials of Examples 9-14 were obtained.

The process was carried out in a manner similar to that in Example 9, except that a mixture of the compound represented by formula (1) and the compound represented by formula (2), in which the ratio of the compound represented by formula (1) is 10.0% by mass, was used instead of the mixture of Example 2 comprising 4-mercaptomethyl-1,8-dimercapto-3,6-dithiaoctane as the main component, thereby obtaining an optical material of Comparative Example 2. The results are shown in Table 2.

TABLE 2

| Examples | Episulfide (parts by mass) | Mixture (parts by mass) | Ratio of (1) in the mixture (% by mass) | Isocyanate (parts by mass) | Distortion |
|---|---|---|---|---|---|
| Example 9 | 77.0 | 14.0 | 0.001 | 9.0 | C |
| Example 10 | 77.0 | 14.0 | 0.005 | 9.0 | B |
| Example 11 | 77.0 | 14.0 | 0.01 | 9.0 | A |
| Example 12 | 77.0 | 14.0 | 1.5 | 9.0 | A |
| Example 13 | 77.0 | 14.0 | 3.0 | 9.0 | B |
| Example 14 | 77.0 | 14.0 | 5.0 | 9.0 | C |
| Comparative Example 2 | 77.0 | 14.0 | 10.0 | 9.0 | D |

The invention claimed is:

1. A thiol compound represented by formula (1):

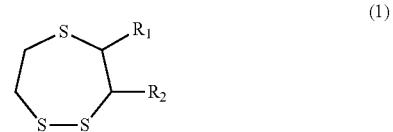

(1)

wherein $R_1$ is $CH_2SCH_2CH_2SH$ and $R_2$ is hydrogen.

2. A method for producing the thiol compound represented by formula (1) according to claim 1, comprising subjecting SH groups in a compound represented by formula (2) to disulfidation by means of an intramolecular reaction using a halogen compound and a basic compound:

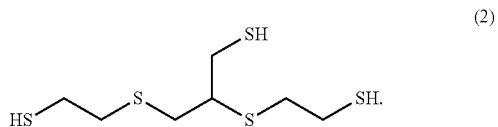 [SMILES: SCCSCC(CS)SCCS]

(2)

3. A mixture of the thiol compound according to claim 1 and a compound represented by formula (2), wherein the ratio of the thiol compound according to claim 1 is 0.001 to 5.0% by mass:

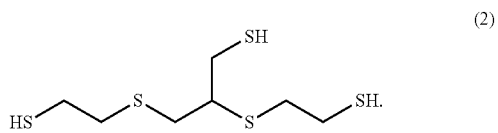 [SMILES: SCCSCC(CS)SCCS]

(2)

4. A composition for optical materials, which comprises the mixture according to claim 3 and at least one of a polyisocyanate compound and an episulfide compound.

5. A method for producing an optical material, which comprises adding a polymerization catalyst to the composition for optical materials according to claim 4 in an amount of 0.0001 to 10% by mass relative to the total amount of the composition for optical materials to polymerize and cure the composition.

6. An optical material obtained by the production method according to claim 5.

7. An optical lens comprising the optical material according to claim 6.

* * * * *